(12) United States Patent
Garrison

(10) Patent No.: US 8,795,269 B2
(45) Date of Patent: Aug. 5, 2014

(54) ROTARY TISSUE SEALER AND DIVIDER

(75) Inventor: David M. Garrison, Longmont, CO (US)

(73) Assignee: Covidien LP, Mansfield, MA (US)

( * ) Notice: Subject to any disclaimer, the term of this patent is extended or adjusted under 35 U.S.C. 154(b) by 1044 days.

(21) Appl. No.: 12/843,384

(22) Filed: Jul. 26, 2010

(65) Prior Publication Data

US 2012/0022532 A1 Jan. 26, 2012

(51) Int. Cl.
*A61B 18/14* (2006.01)
(52) U.S. Cl.
USPC .............................. 606/37; 606/45
(58) Field of Classification Search
USPC ...................................... 606/32–52
See application file for complete search history.

(56) References Cited

U.S. PATENT DOCUMENTS

| D249,549 S | 9/1978 | Pike |
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| 5,623,018 A | 4/1997 | Ohmae et al. |
| D384,413 S | 9/1997 | Zlock et al. |
| 5,669,906 A * | 9/1997 | Grossi et al. ................ 606/46 |
| 5,766,215 A * | 6/1998 | Muri et al. .................. 606/46 |
| D402,028 S | 12/1998 | Grimm et al. |
| 5,893,884 A | 4/1999 | Tu |
| D416,089 S | 11/1999 | Barton et al. |
| D424,694 S | 5/2000 | Tetzlaff et al. |
| D425,201 S | 5/2000 | Tetzlaff et al. |
| 6,190,383 B1 | 2/2001 | Schmaltz et al. |
| D449,886 S | 10/2001 | Tetzlaff et al. |
| D454,951 S | 3/2002 | Bon |
| D457,958 S | 5/2002 | Dycus et al. |
| D457,959 S | 5/2002 | Tetzlaff et al. |

(Continued)

FOREIGN PATENT DOCUMENTS

| DE | 2415263 | 10/1975 |
| DE | 2514501 | 10/1976 |

(Continued)

OTHER PUBLICATIONS

Michael Choti, "Abdominoperineal Resection with the LigaSure Vessel Sealing System and LigaSure Atlas 20 cm Open Instrument"; Innovations That Work, Jun. 2003.

(Continued)

*Primary Examiner* — Linda Dvorak
*Assistant Examiner* — Jocelyn D Ram

(57) ABSTRACT

A surgical instrument includes an end effector assembly defining a feed-in side. The end effector assembly includes first and second rotatable gear members positioned adjacent one another to define a gap therebetween. When the first and second gear members are rotated, tissue positioned adjacent the feed-in side of the end effector assembly is engaged by the first and second gear members and is fed into the gap between the first and second gear members for one or both of sealing and dividing tissue disposed between the first and second gear members.

22 Claims, 11 Drawing Sheets

(56) References Cited

U.S. PATENT DOCUMENTS

| | | |
|---|---|---|
| 6,382,968 B2 | 5/2002 | Livaditis |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| 8,070,748 B2 | 12/2011 | Hixson et al. |
| 8,092,451 B2 | 1/2012 | Schechter et al. |
| 8,112,871 B2 | 2/2012 | Brandt et al. |
| 8,114,076 B2 * | 2/2012 | Markham ................ 606/52 |
| 8,133,254 B2 | 3/2012 | Dumbauld et al. |
| 8,162,965 B2 | 4/2012 | Reschke et al. |
| 8,187,273 B2 | 5/2012 | Kerr et al. |
| 8,215,182 B2 | 7/2012 | Artale et al. |
| 8,257,352 B2 | 9/2012 | Lawes et al. |
| 8,266,783 B2 | 9/2012 | Brandt et al. |
| 8,287,536 B2 | 10/2012 | Mueller et al. |
| 8,292,886 B2 | 10/2012 | Kerr et al. |
| 8,298,229 B2 * | 10/2012 | Kano et al. ................ 606/48 |
| 8,298,233 B2 | 10/2012 | Mueller |
| 8,323,310 B2 | 12/2012 | Kingsley |
| 8,343,150 B2 | 1/2013 | Artale |
| 8,343,151 B2 | 1/2013 | Siebrecht et al. |
| 8,348,948 B2 | 1/2013 | Bahney |
| 8,357,159 B2 | 1/2013 | Romero |
| 8,388,647 B2 | 3/2013 | Nau, Jr. et al. |
| 8,409,246 B2 | 4/2013 | Kerr et al. |
| 8,409,247 B2 | 4/2013 | Garrison et al. |
| 8,425,511 B2 | 4/2013 | Olson |
| 8,430,876 B2 | 4/2013 | Kappus et al. |
| 8,430,877 B2 | 4/2013 | Kerr et al. |
| 8,439,911 B2 | 5/2013 | Mueller |
| 8,439,913 B2 | 5/2013 | Horner et al. |
| 8,469,991 B2 | 6/2013 | Kerr |
| 8,469,992 B2 | 6/2013 | Roy et al. |
| 8,480,671 B2 | 7/2013 | Mueller |
| 8,491,624 B2 | 7/2013 | Kerr et al. |
| 8,491,625 B2 | 7/2013 | Horner |
| 8,491,626 B2 | 7/2013 | Roy et al. |
| 8,512,336 B2 | 8/2013 | Couture |
| 8,512,371 B2 | 8/2013 | Kerr et al. |
| 8,540,749 B2 | 9/2013 | Garrison et al. |
| 8,556,929 B2 | 10/2013 | Harper et al. |
| 8,568,397 B2 | 10/2013 | Horner et al. |
| 8,568,412 B2 | 10/2013 | Brandt et al. |
| 8,585,736 B2 | 11/2013 | Horner et al. |
| 8,597,295 B2 | 12/2013 | Kerr |
| 8,641,712 B2 | 2/2014 | Couture |
| 8,641,713 B2 | 2/2014 | Johnson et al. |
| 8,652,135 B2 | 2/2014 | Nau et al. |
| 2003/0018332 A1 | 1/2003 | Schmaltz et al. |
| 2008/0208190 A1 * | 8/2008 | Hashiguchi et al. ............ 606/43 |
| 2009/0018535 A1 * | 1/2009 | Schechter et al. ............. 606/33 |
| 2009/0306541 A1 * | 12/2009 | Kano et al. .................... 600/564 |
| 2010/0016853 A1 * | 1/2010 | Burbank ......................... 606/48 |
| 2010/0094286 A1 * | 4/2010 | Chojin ............................. 606/51 |
| 2010/0204697 A1 | 8/2010 | Dumbauld et al. |
| 2010/0204698 A1 | 8/2010 | Chapman et al. |
| 2010/0217258 A1 | 8/2010 | Floume et al. |
| 2010/0249769 A1 | 9/2010 | Nau, Jr. et al. |
| 2010/0249776 A1 | 9/2010 | Kerr |
| 2010/0274244 A1 | 10/2010 | Heard |
| 2010/0280511 A1 | 11/2010 | Rachlin et al. |
| 2010/0286691 A1 * | 11/2010 | Kerr et al. ...................... 606/51 |
| 2010/0307934 A1 | 12/2010 | Chowaniec et al. |
| 2010/0312238 A1 * | 12/2010 | Schechter et al. .............. 606/33 |
| 2010/0331839 A1 | 12/2010 | Schechter et al. |
| 2011/0034918 A1 | 2/2011 | Reschke |
| 2011/0046623 A1 | 2/2011 | Reschke |
| 2011/0054468 A1 | 3/2011 | Dycus |
| 2011/0054471 A1 | 3/2011 | Gerhardt et al. |
| 2011/0060335 A1 | 3/2011 | Harper et al. |
| 2011/0071523 A1 | 3/2011 | Dickhans |
| 2011/0073594 A1 | 3/2011 | Bonn |
| 2011/0077648 A1 | 3/2011 | Lee et al. |
| 2011/0118736 A1 | 5/2011 | Harper et al. |
| 2011/0190765 A1 | 8/2011 | Chojin |
| 2011/0193608 A1 | 8/2011 | Krapohl |
| 2011/0218530 A1 | 9/2011 | Reschke |
| 2011/0230880 A1 | 9/2011 | Chojin et al. |
| 2011/0251605 A1 | 10/2011 | Hoarau et al. |
| 2011/0270245 A1 | 11/2011 | Horner et al. |
| 2011/0270251 A1 | 11/2011 | Horner et al. |
| 2011/0276048 A1 | 11/2011 | Kerr et al. |
| 2011/0276049 A1 | 11/2011 | Gerhardt |
| 2011/0295251 A1 | 12/2011 | Garrison |
| 2011/0295313 A1 | 12/2011 | Kerr |
| 2011/0319886 A1 | 12/2011 | Chojin et al. |
| 2011/0319888 A1 | 12/2011 | Mueller et al. |
| 2012/0004658 A1 * | 1/2012 | Chojin ............................ 606/46 |
| 2012/0022532 A1 | 1/2012 | Garrison |
| 2012/0035606 A1 * | 2/2012 | Kano et al. ..................... 606/45 |
| 2012/0041438 A1 | 2/2012 | Nau, Jr. et al. |
| 2012/0046662 A1 | 2/2012 | Gilbert |
| 2012/0059371 A1 | 3/2012 | Anderson et al. |
| 2012/0059372 A1 | 3/2012 | Johnson |
| 2012/0059374 A1 | 3/2012 | Johnson et al. |
| 2012/0059375 A1 | 3/2012 | Couture et al. |
| 2012/0059408 A1 | 3/2012 | Mueller |
| 2012/0059409 A1 | 3/2012 | Reschke et al. |
| 2012/0083785 A1 | 4/2012 | Roy et al. |
| 2012/0083786 A1 | 4/2012 | Artale et al. |
| 2012/0083827 A1 | 4/2012 | Artale et al. |

FOREIGN PATENT DOCUMENTS

| | | |
|---|---|---|
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10045375 | 10/2002 |
| DE | 10 2004 026179 | 12/2005 |
| DE | 20 2007 009317 | 10/2007 |
| DE | 19738457 | 1/2009 |
| EP | 1159926 | 12/2001 |
| JP | 61-501068 | 9/1984 |
| JP | 65-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |

(56) References Cited

FOREIGN PATENT DOCUMENTS

| | | |
|---|---|---|
| JP | 08252263 | 10/1996 |
| JP | 09010223 | 1/1997 |
| JP | 10-24051 | 1/1998 |
| JP | 11-070124 | 5/1998 |
| JP | 2000-102545 | 9/1998 |
| JP | 11-169381 | 6/1999 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| RU | 401367 | 11/1974 |
| WO | WO 00/36986 | 6/2000 |
| WO | WO 01/54604 | 8/2001 |
| WO | WO 2005/110264 | 11/2005 |

OTHER PUBLICATIONS

Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967, British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan., 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct., 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.

Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan., 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.

(56) References Cited

OTHER PUBLICATIONS

Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 157500.9 dated Jul. 30, 2010.
Int'l Search Report EP 10 159205.3 dated Jul. 7, 2010.
Int'l Search Report EP 10 160870,1 dated Aug. 9, 2010.
Int'l Search Report EP 10 161596.1 dated Jul. 28, 2010.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
U.S. Appl. No. 09/387,883, filed Sep. 1, 1999, Schmaltz et al.
U.S. Appl. No. 09/591,328, filed Jun. 9, 2000, Ryan et al.
U.S. Appl. No. 12/336,970, filed Dec. 17, 2008, Sremcich et al.

* cited by examiner

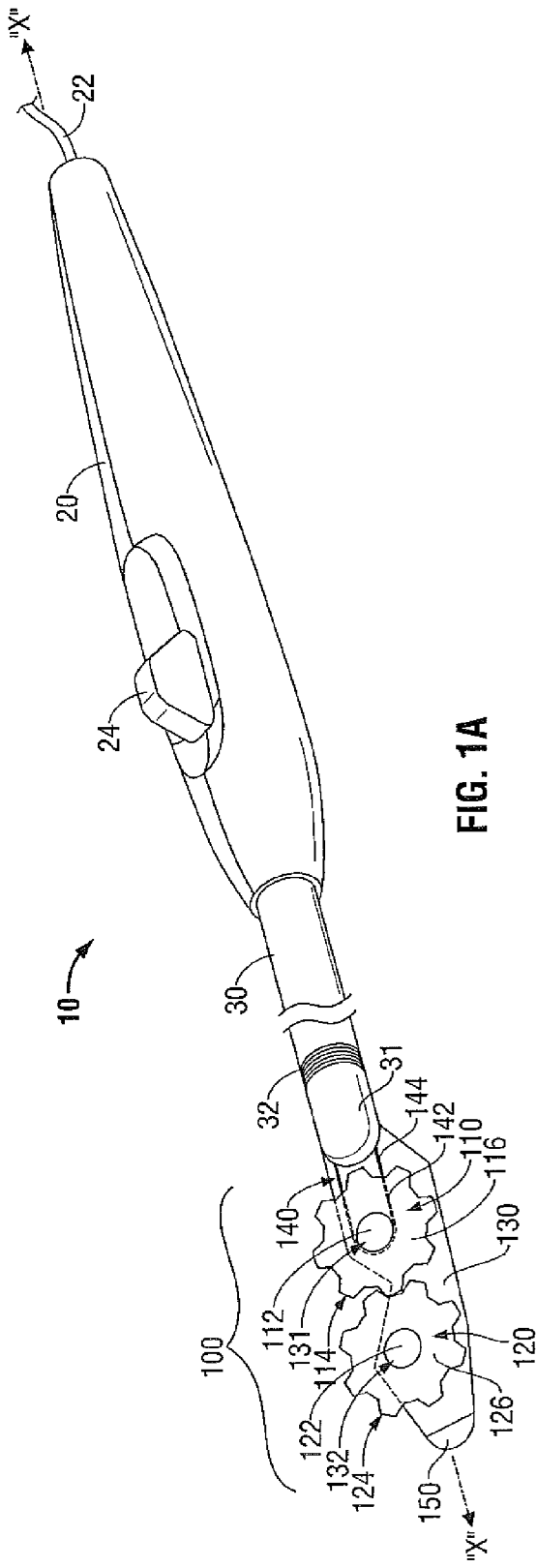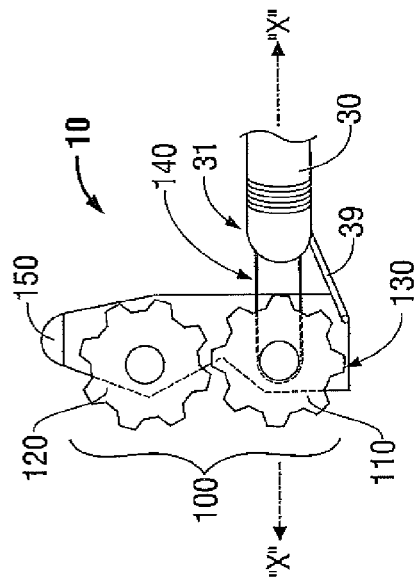

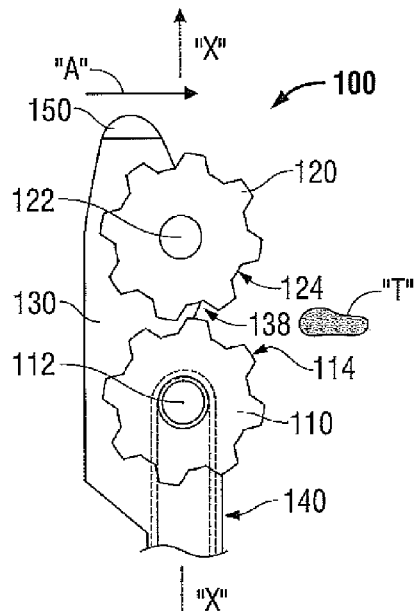
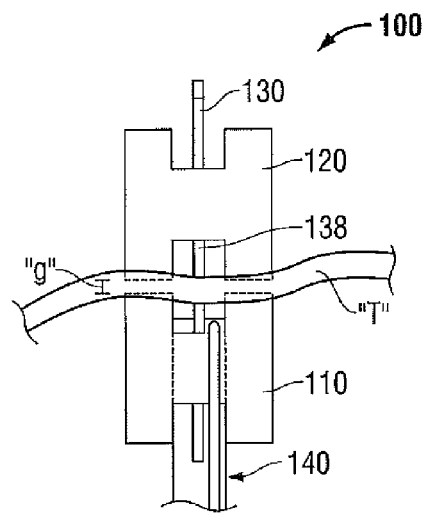
FIG. 6A     FIG. 6B
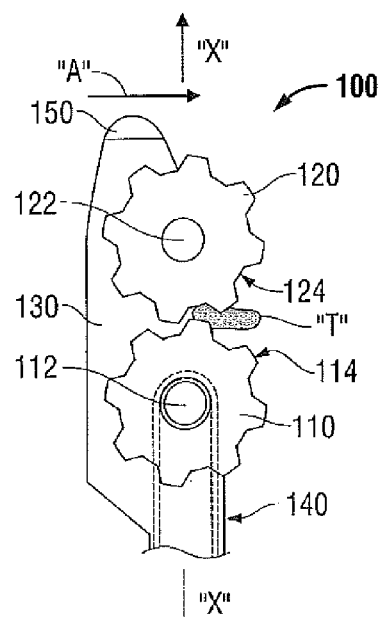
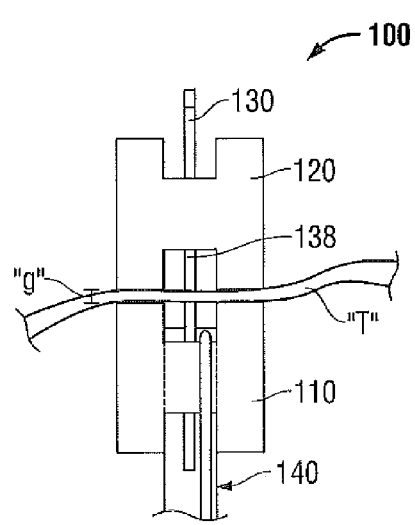
FIG. 7A     FIG. 7B

ROTARY TISSUE SEALER AND DIVIDER

BACKGROUND

The present disclosure relates to surgical devices. More particularly, the present disclosure relates to a surgical instrument for sealing and dividing tissue.

TECHNICAL FIELD

Electrosurgical instruments, e.g., electrosurgical forceps, utilize both mechanical clamping action and electrical energy to effect hemostasis by heating tissue and blood vessels to coagulate, cauterize and/or seal tissue. Typically, once a vessel is sealed, the surgeon has to accurately sever the vessel along the newly formed tissue seal. Accordingly, many vessel sealing instruments have been designed which incorporate a knife or blade member which effectively severs the tissue after forming a tissue seal.

In use, the vessel to be sealed and divided is typically grasped between opposing jaw members of the forceps. Next, by applying electrical energy between the jaw members, the surgeon seals the tissue by controlling the intensity, frequency and duration of the electrosurgical energy applied through the jaw members to the tissue. Finally, once the vessel or tissue is sealed, the surgeon advances a knife to sever the sealed tissue disposed between the opposing jaw members. Put more generally, electrosurgical forceps employ a three-step process for sealing and dividing tissue: a clamping, or grasping step, an energy applying, or sealing step, and a cutting step.

SUMMARY

The present disclosure relates to a surgical instrument including an end effector assembly. The end effector assembly defines a feed-in side and includes first and second gear members positioned adjacent to one another to define a gap therebetween. When the gear members are rotated, tissue positioned adjacent to the feed-in side of the end effector assembly is engaged by the first and second gear members and is fed into the gap between the first and second gear members to seal and/or divide tissue disposed between the gear members.

In one embodiment, one (or both) of the gear members is adapted to connect to a source of electrosurgical energy. More particularly, a first electrical potential may be provided to the first gear member and a second electrical potential may be provided to the second gear member such that energy may be conducted between the gear members and through tissue disposed therebetween to effect a tissue seal.

In another embodiment, one (or both) of the gear members includes an electrically-insulative material disposed on a portion of an outer periphery thereof to maintain the gap defined between the first and second gear members.

In yet another embodiment, the first and second gear members define complementary outer peripheral configurations.

In still another embodiment, the end effector assembly includes a base plate interconnecting the first and second gear members. The base plate may define a cutting edge extending between the first and second gear members for cutting tissue disposed therebetween. The base plate may also include a dissecting distal tip adapted to connect to a source of electrosurgical energy for dissecting, or cutting through tissue upon distal advancement of the end effector assembly.

In still yet another embodiment, the surgical instrument includes a handle assembly having a shaft extending distally therefrom. The end effector assembly is disposed at the distal end of the shaft. The end effector assembly may also be configured to articulate and/or rotate with respect to the handle assembly.

In another embodiment, a drive assembly is coupled to one (or both) of the gear members for rotating the first and second gear members. The drive assembly may include a drive cable coupled to an axle of the first gear member for rotating the first gear member in a forward and/or a reverse direction. The first and second gear members may be meshed with one another such that rotation of the first gear member, e.g., by the drive cable of the drive assembly, effects rotation of the second gear member.

In yet another embodiment, a cutting belt is disposed between the first and second gear members. The cutting belt is positioned about the axles of the first and second gear members and is configured to cut tissue disposed between the gear members. The cutting belt may define a straight cutting edge or a serrated cutting edge and/or may be expandable.

In still yet another embodiment, the end effector assembly may be configured such that the gap between the first and second gear members defines a length in the range of about 0.001 inches to about 0.008 inches. Further, the pressure exerted on tissue grasped between the gear members may be in the range of about 3 kg/cm$^2$ to about 16 kg/cm$^2$.

In accordance with the present disclosure, another embodiment of a surgical instrument is provided. The surgical instrument includes an end effector assembly defining a longitudinal axis and a feed-in side. The end effector assembly includes a base plate extending along the longitudinal axis and defining a proximal end and a distal end. First and second gear members are rotatably mounted on the base plate and are configured for sealing and/or dividing tissue disposed between the first and second gear members. The base plate is configured for maintaining the first and second gear members is a spaced-apart configuration relative to one another to define a gap distance therebetween and/or for maintaining a pressure on tissue grasped between the gear members.

In one embodiment, a first electrical potential may be provided to the first gear member and a second electrical potential may be provided to the second gear member such that energy is conducted between the gear members and through tissue disposed therebetween to effect a tissue seal.

In another embodiment, the base plate defines a cutting edge extending between the first and second gear members for cutting tissue disposed therebetween. The base plate may also include a dissecting distal tip adapted to connect to a source of electrosurgical energy.

In yet another embodiment, a drive assembly is coupled to the first and/or second gear member for rotating the first and second gear members.

In still another embodiment, each of the first and second gear members defines a bifurcated configuration such that the base plate extends between each of the bifurcated gear members.

In still yet another embodiment, the base plate includes one or more compliance features configured for adjusting the gap distance between the gear members and/or the pressure exerted on tissue grasped between the gear members according to tissue grasped therebetween, e.g., according to the size and/or composition of tissue grasped therebetween.

BRIEF DESCRIPTION OF THE DRAWINGS

Various embodiments of the presently disclosed surgical instrument are described herein with reference to the drawings, wherein:

FIG. 1A is a side, perspective view of a surgical instrument in accordance with the present disclosure;

FIG. 1B is a side, perspective view of an end effector assembly if FIG. 1A shown in an articulated position;

FIG. 6A is a side view of the end effector assembly of FIG. 4 shown positioned adjacent tissue to be sealed;

FIG. 6B is a top view of the end effector assembly of FIG. 4 shown positioned adjacent tissue to be sealed;

FIG. 7A is a is a side view of the end effector assembly of FIG. 4 where the rotating gear members are feeding tissue into the gap therebetween;

FIG. 7B is a is a top view of the end effector assembly of FIG. 4 where the rotating gear members are feeding tissue into the gap therebetween;

DETAILED DESCRIPTION

Figure 2:
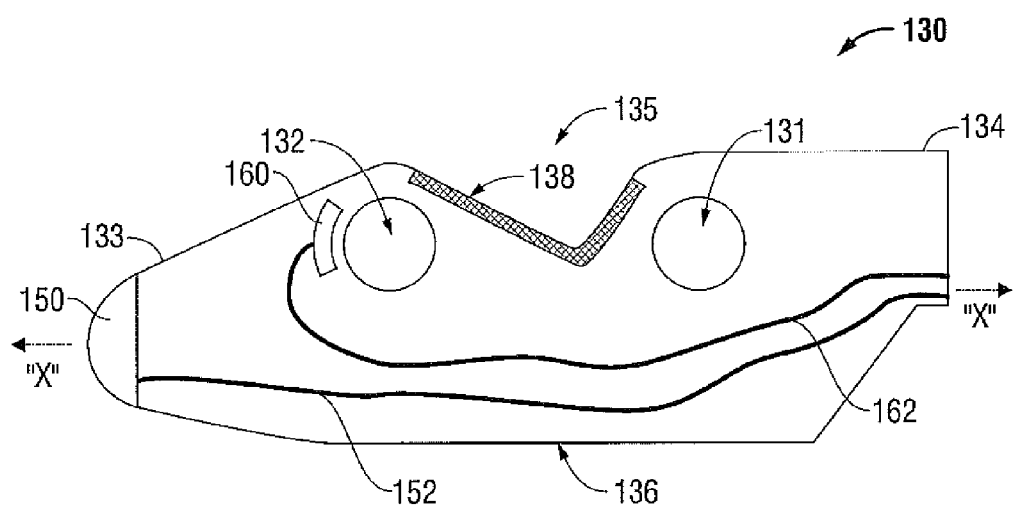
FIG. 2 is a side view of one embodiment of a base plate for use with the surgical instrument of FIG. 1A.

Embodiments of the presently disclosed surgical instrument are described in detail with reference to the drawing figures wherein like reference numerals identify similar or identical elements. As used herein, the term "distal" refers to the portion that is being described which is further from a user, while the term "proximal" refers to the portion that is being described which is closer to a user.

Referring now to FIGS. 1A-1B, a surgical instrument for sealing and dividing tissue is shown generally identified by reference numeral 10. Surgical instrument 10 includes a handle assembly 20 having a shaft 30 extending distally therefrom and an end effector assembly 100 disposed at a distal end 31 of shaft 30, although surgical instrument 10 need not be a shaft-based instrument. Handle assembly 20 is adapted to connect to a source of energy, e.g., via an insulated electrosurgical cable 22, for powering surgical instrument 10 and/or for supplying electrosurgical energy to end effector assembly 100 for sealing tissue, as will be described in greater detail below. Handle assembly 20 houses the internal components of surgical instrument 10 and includes an actuator, or switch 24 disposed thereon for controlling the operation of surgical instrument 10, e.g., for activating/deactivating surgical instrument 10. Additional controls (not shown) may be provided, for example, for switching between various modes of operation. Surgical instrument 10 may alternatively be configured as a battery-powered device, obviating the need for electrosurgical cable 22. In such an embodiment, a battery pack (not shown) disposed within handle assembly 20 provides power to surgical instrument 10.

As mentioned above, shaft 30 extends distally from handle assembly 20 along longitudinal axis "X-X." Shaft 30 may include an articulating section 32 configured to permit distal end 31 of shaft 30 and, thus, end effector assembly 100, to bend, or articulate with respect to longitudinal axis "X-X." Alternatively, as shown in FIG. 1B, end effector assembly 100 may be pivotably coupled to shaft 30 and may include a pivoting linkage 39 extending therebetween for permitting end effector assembly 100 to be articulated with respect to longitudinal axis "X-X" from about 0 degrees (FIG. 1A) to about 90 degrees (FIG. 1B). Further, shaft 30 may be configured to rotate about longitudinal axis "X-X" with respect to handle assembly 20 such that end effector assembly 100 may be rotated with respect to handle assembly 20.

Figure 5:
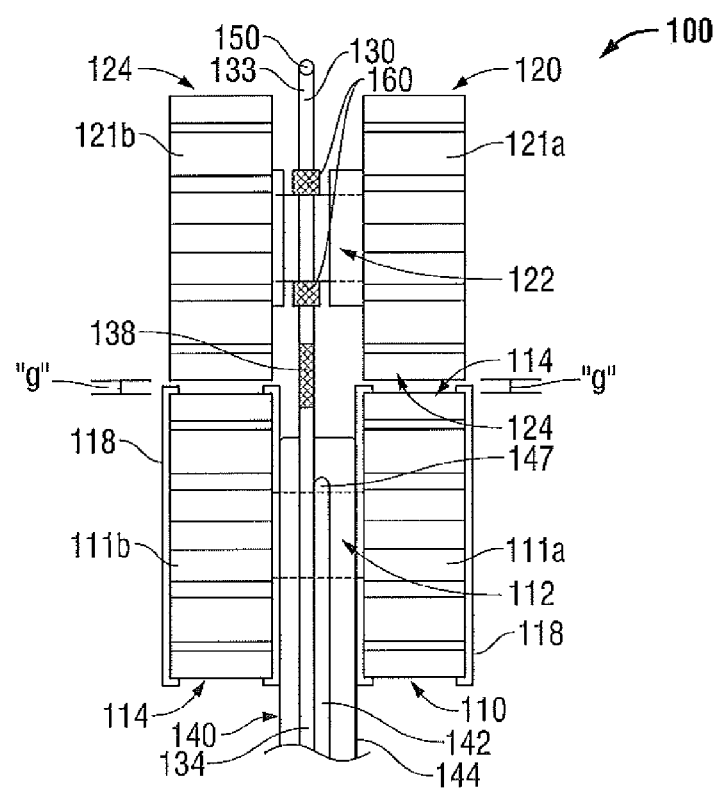
FIG. 5 is a top view of the end effector assembly of FIG. 4.

With continued reference to FIGS. 1A-1B, end effector assembly 100 includes first and second wheels, or gear members 110, 120 positioned end-to-end with respect to one another along longitudinal axis "X-X." Gear members 110, 120 are rotatably mounted to a base plate 130. More particularly, each gear member 110, 120 includes a pair of gear halves 111a, 111b and 121a, 121b (see FIG. 5), respectively, disposed on opposing ends of respective gear axles 112, 122 (see FIG. 5). Gear axles 112, 122 extend through apertures 131, 132, respectively, defined within base plate 130 to mount gear members 110, 120 about base plate 130, i.e., such that base plate 130 extends between gear halves 111a, 111b of first gear member 110 and gear halves 121a, 121b of second gear member 120 (FIG. 5). Base plate 130 is engaged to distal end 31 of shaft 30.

As shown in FIG. 1A, first, or proximal gear member 110 is positioned adjacent distal end 31 of shaft 30, while second, or distal gear member 120 is positioned distally of first gear member 110 along longitudinal axis "X-X." Gear axles 112, 122 of gear members 110, 120, respectively, are substantially parallel with respect to one another and are spaced apart a sufficient distance such that gear members 110, 120 are in an interfitting, or meshed engagement with respect to one another. Due to this interfitting, or meshed configuration, rotation of first gear member 110 effects similar rotation of second gear member 120, and vice versa. Accordingly, only one gear, e.g., first gear member 110, need be coupled to a drive assembly, e.g., drive assembly 140, for rotating gear members 110, 120 with respect to base plate 130. However, both gear members 110, 120 may be coupled to drive assembly 140 for powered rotation of each of gear members 110, 120.

Drive assembly 140 extends distally from shaft 30 to engage first gear member 110 (and/or second gear member 120). More specifically, drive assembly 140 includes a drive cable 142 that is disposed about axle 112 of gear member 110 and extends proximally through shaft 30, ultimately coupling to a drive mechanism (not shown) that drives the rotation of gear member 110 which, in turn, rotates gear member 120. Drive shaft 144 similarly extends distally from shaft 30 and houses drive cable 142 and gear axle 112 of gear member 110 therein. As can be appreciated, drive shaft 144 protects drive cable 142 and gear axle 112 from fluids, debris, tissue, or other substances that may interfere with the operation of drive assembly 140. The specific configuration and operation of drive assembly 140 will be described in greater detail below.

Continuing with reference to FIG. 1A, gear members 110, 120 each define an electrically conductive sealing surface 114, 124, respectively, on an outer circumference thereof. In other words, the outwardly-facing circumferential surfaces of gear members 110, 120, which each define a symmetrically alternating cogged and recessed configuration, i.e., a "geared" configuration, are formed from an electrically-conductive material. Alternatively, gear members 110, 120 may each include a sealing plate (not shown) disposed about the outer circumference thereof and shaped to accommodate the alternating cogs and recesses of gear members 110, 120. Although cogged gear members 110, 120 are shown, gear members 110, 120 may be configured to include V-shaped teeth, "paddle" teeth, a rough-textured surface, or may be configured in any other suitable arrangement.

The body portions 116, 126, of gear members 110, 120, respectively, may be formed from an electrically-insulative, or non-conductive material, or may be enclosed within an insulative housing (in which case body portions 116, 126 of gear members 110, 120, respectively, may be formed from an electrically conductive material). Axles 112, 122 are electrically coupled to respective gear members 110, 120, e.g., via electrodes (not shown) or via body portions 116, 126 (in embodiments where body portions 116, 126 of gear members 110, 120, respectively, are formed from an electrically conductive material disposed within an insulative housing), for conducting electrosurgical energy to sealing surfaces 114, 124 of gear members 110, 120, respectively. As will be described below, axle 112 and/or axle 122 are connected to a source of energy, e.g., via electrosurgical cable 22, and, thus, serve as a conduit for supplying energy to sealing surfaces 114, 124 of gear members 110, 120, respectively.

With reference now to FIG. 2, base plate 130 is shown including a distal end 133, a proximal end 134, a feed-in side 135, and a feed-out side 136. Base plate 130 may be formed from any suitable bio-compatible material. As mentioned above, base plate 130 includes a pair of apertures 131, 132 defined therein and configured to receive axles 112, 122 of gear members 110, 120, respectively, therethrough (FIG. 1A). Base plate 130 further defines a cutting edge 138 disposed between apertures 131, 132 and extending along feed-in side 135 of base plate 130 for cutting tissue disposed between, i.e., fed into the gap between gear members 110, 120 (FIG. 1A). Base plate 130 may define a relatively flat configuration such that, as will be described in greater detail below, as end effector assembly 100 is advanced transversely with respect to tissue, tissue is initially fed into, or grasped by gear members 110, 120 and is sealed between gear members 110, 120 (FIG. 1A). Tissue is then cut, or divided along the tissue seal by cutting edge 138 of base plate 130 as it is fed into contact with cutting edge 138 by the rotation of gear members 110, 120. End effector assembly 100 is ultimately passed completely through tissue, with base plate 130 translating between the sealed and divided tissue segments.

Base plate 130 may also include a dissecting, or cutting electrode 150 disposed on a distal end 133 thereof. More specifically, the dissecting electrode 150 extends distally from base plate 130 along longitudinal axis "X-X" to form the distal tip of base plate 130. Dissecting electrode 150 is electrically coupled, e.g., via lead cable 152, to a source of electrosurgical energy for energizing dissecting electrode 150. Dissecting electrode 150 may be configured as a monopolar or a bipolar electrode. When activated, dissecting electrode 150 may be used for dynamic electrical dissection, or cutting of tissue as end effector assembly 100 is advanced through tissue, e.g., vertically or axially relative to longitudinal axis "X-X," to reach the target location. Lead cable 152 may be recessed within, or may be completely disposed within base plate 130 such that lead cable 152 does not protrude from base plate 130. Lead cable 152 may also include an insulative coating, or cover (not shown) such that dissecting electrode 150 is electrically isolated from the other components of end effector assembly 100. Accordingly, dissecting electrode 150 may be controlled (i.e., activated and deactivated) independently of gear members 110, 120 of end effector assembly 100 (FIG. 1A). In other words, end effector assembly 100 may be configured for use in two independent modes: a cutting/dissecting mode, wherein dissection electrode 150 is activated, and a tissue sealing/dividing mode, wherein, as will be described in greater detail below, gear members 110, 120 are activated. However, end effector assembly 100 may also be configured to operate in each of the dissection and sealing/cutting modes simultaneously.

With continued reference to FIG. 2, in conjunction with FIG. 1A, base plate 130 may include one or more brush contacts 160 positioned adjacent aperture 132 (and/or may include a second brush contact (not shown) positioned adjacent aperture 131). Brush contact 160 is configured to contact second gear member 120, and, more specifically, axle 122 of gear member 120, for conducting electrosurgical energy therebetween. As mentioned above, due to the electrical coupling of axles 112, 122 and sealing surfaces 114, 124, of gear members 110, 120, respectively, brush contact 160 is capable of energizing sealing surface 124 of second gear member 120. Accordingly, lead cable 162, which may be similar to lead cable 152 described above, electrically couples brush contact 160 and, thus, second gear member 120, to a source of electrosurgical energy for supplying energy to sealing surface 124 of second gear member 120. A second brush contact (not shown) and corresponding lead cable (not shown), similar to brush contact 160 and lead cable 162, respectively, may be provided for energizing sealing surface 114 of first gear member 110.

Alternatively, sealing surface 114 of first gear member 110 may be supplied with energy via drive assembly 140 and, more specifically, via electrical communication between drive cable 142 and axle 112 of gear member 110. In other words, due to the electrical communication between axle 112 and sealing surface 114 of gear member 110, electrical energy may be supplied to sealing surface 114 of gear member 110 via conduction through drive cable 142 (which extends into shaft 30, ultimately coupling to a source of electrosurgical energy, e.g., electrosurgical cable 22 (FIG. 1A)) and axle 112. In either configuration, a first electrical potential may be provided to sealing surface 114 of first gear member 110 and a second, different electrical potential may be provided to sealing surface 124 of second gear member 120 such that an electrical potential gradient is created for conducting energy between the gear members 110, 120 (FIG. 1) and through tissue therebetween for effecting a tissue seal.

Figure 3:
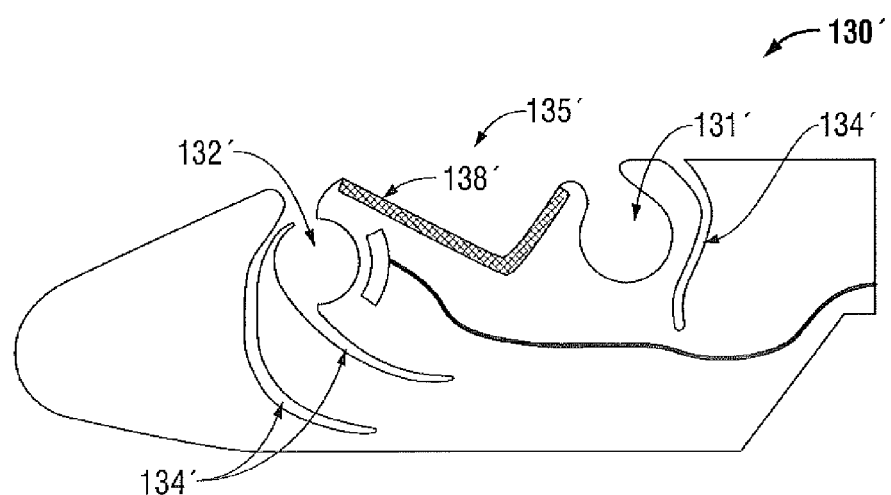
FIG. 3 is a side view of another embodiment of a base plate for use with the surgical instrument of FIG. 1A.

With reference now to FIG. 3, another embodiment of a base plate, base plate 130', is shown. Base plate 130' is similar to base plate 130 (FIG. 2) and includes first and second apertures 131', 132' defined therein and configured to receive axles 112, 122 of gear members 110, 120, respectively, therethrough (FIG. 1A). Base plate 130' also includes a cutting edge 138' extending along feed-in side 135' and between apertures 131', 132' of base plate 130'. Base plate 130' may further include one or more elongated channels 134' defined therein. Elongated channels 134' defined within base plate 130' allow for some degree of compliance, or flexibility of base plate 130', for maintaining the integrity and alignment of base plate 130' and, more particularly, of gear members 110, 120 (FIG. 1A) mounted on base plate 130'. Similarly, each of apertures 131', 132' may include an open mouth, as shown in FIG. 3, for providing flexibility to base plate 130', while securely retaining axles 112, 122 of gear members 110, 120 (FIG. 1A), respectively, therethrough. Elongated channels 134' and the open mouths of apertures 131', 132' also help maintain the gap distance between gear members 110, 120 as a function of the pressure exerted on base plate 130', thus permitting base plate 130' to adapt to various configurations, e.g., tissue of varying size and/or composition. Other configurations and/or features may also be provided to help maintain the alignment and integrity of end effector assembly 100 during assembly, storage, and/or use.

Figure 4:
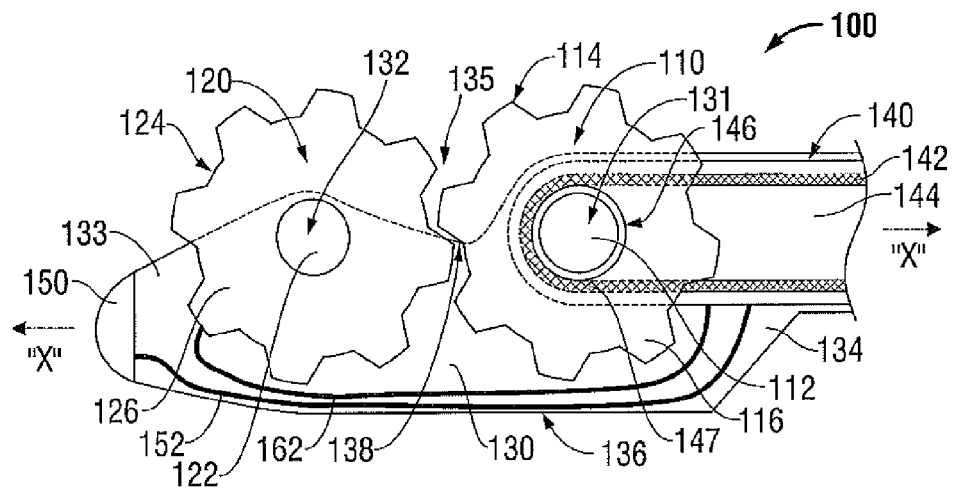
FIG. 4 is a side, cross-sectional view of one embodiment of an end effector assembly for use with the surgical instrument of FIG. 1A.

Referring now to FIGS. 4 and 5, end effector assembly 100 is shown assembled and configured for use. As best shown in FIG. 4, gear members 110, 120 are mounted on base plate 130 (through apertures 131, 132, respectively) with cutting edge 138 of base plate 130 extending between gear members 110, 120. More specifically, gear halves 111a, 121a of gear members 110, 120, respectively, are disposed on one side of base plate 130, while gear halves 111b, 121b of respective gear members 110, 120 are disposed on the other side of base plate 130. In other words, gears 110, 120 define a bifurcated configuration with base plate 130 extending between the bifurcated gear members 110, 120. Gear axles 112, 122 of gear members 110, 120, respectively, as mentioned above, extend through apertures 131, 132, respectively, of base plate 130, interconnecting gear halves 111a, 111b of gear member 110 and gear halves 121a, 121b of gear member 120. As mentioned above, gear axles 112, 122 of gear members 110, 120, respectively, when mounted on base plate 130, are substantially parallel to one another and are spaced-apart a sufficient distance with respect to one another such that gear members 110, 120 are in meshed engagement with one another, i.e., such that rotation of gear member 110 effects similar rotation of gear member 120.

When gear members 110, 120 are in an at-rest, or stationary position, as shown in FIGS. 4 and 5, a gap distance "g" is defined between sealing surfaces 114, 124 of respective gear members 110, 120. However, due to the meshed engagement of gear members 110, 120, e.g., the cogged/recessed configuration of gear members 110, 120, gear members 110, 120 are moved into contact with one another upon rotation of gear members 110, 120. Accordingly, as best shown in FIG. 5, gear member 110 (and/or gear member 120) may include an insulative sleeve, or jacket 118 disposed on an outer periphery thereof for maintaining the gap distance "g" between sealing surfaces 114, 124 of gear members 110, 120, respectively, during rotation of gear members 110, 120. Alternatively, in embodiments where gear members 110, 120 are independently driven by a drive assembly, e.g., drive assembly 140, gear members 110, 120 may be configured to rotate complementarily to one another, to maintain the gap distance "g" between sealing surfaces 114, 124 of gear members 110, 120 during rotation of gear members 110, 120, or may also include an insulative sleeve 118 disposed thereon. In other words, rotation of gear member 110 may be offset relative to rotation of gear member 120 to prevent the cogs of gear members 110, 120 from contacting one another during rotation of gear members 110, 120. Maintaining the gap distance "g" between sealing surfaces 114, 124 of gear members 110, 120 is important to help prevent the two electrically conductive surfaces 114, 124 from contacting one another during the tissue sealing process and to help ensure that tissue disposed between gear members 110, 120 is adequately sealed.

With continued reference to FIGS. 4 and 5, and as mentioned above, drive assembly 140 includes a drive cable 142 disposed within a drive shaft 144 and coupled to a drive mechanism (not shown). Drive shaft 144 extends distally from shaft 30 of surgical instrument 10 along longitudinal axis "X-X" (see FIG. 1A) and engages base plate 130 thereto. Aperture 146 defined through drive shaft 144 is aligned with aperture 131 of base plate 130 to permit passage of axle 112 of gear member 110 therethrough. Drive cable 142, which is disposed within drive shaft 144, is formed as a loop and likewise extends from shaft 30 such that distal end 147 of drive cable loop 142 is disposed about axle 112 of gear member 110. More particularly, drive cable loop 142 is operatively engaged to axle 112 of gear member 110 (e.g., via a chain-sprocket engagement, dual-wrapped cable, or other mechanical interlock) such that rotation of drive cable loop 142 rotates, or drives the rotation of axle 112, thereby rotating gear member 110. The proximal end (not shown) of drive cable loop 142 is operatively engaged to the drive mechanism (not shown), e.g., a motor, for powering the rotation of drive cable 142 and, thus, for rotating gear member 110. Other suitable drive mechanisms (not shown) for driving gear member 110 and/or gear member 120 may also be provided in accordance with the present disclosure. Further, drive assembly 140 may be configured to drive the rotation of gear members 110, 120 in both forward and reverse directions and at various rotational speeds, e.g., a low setting, a medium setting and a high setting, or continuously through a range of rotational speeds, e.g., between a minimum and a maximum rotational speed. As will be described in greater detail below, gear members 110, 120 are rotated to engage tissue and to feed tissue into the gap defined therebetween. As tissue is engaged and fed between gear members 110, 120 by the rotation of gear members 110, 120, electrosurgical energy is supplied to sealing surface 114, 124 of gear members 110, 120, respectively, to effect a tissue seal. Upon further rotation of gear members 110, 120, tissue is released, or disengaged as it is fed-out the opposite side of end effector assembly 100. Thus, the slower the rotation of gear members 110, 120, the longer tissue is in contact within sealing surfaces 114, 124 and, thus, the longer electrosurgical energy is conducted through tissue. Accordingly, the selected setting of drive assembly 140, e.g., the low speed setting, the medium speed setting, or the high speed setting, may be based, at least in part, on the required duration of energy application which, ultimately, may depend on the size and/or composition of tissue to be sealed.

Referring now to FIGS. 6A-9B, the operation of surgical instrument 10 will be described. Initially, end effector assembly 100 is advanced into position such that tissue "T" to be sealed and divided is disposed adjacent feed-in side 135 of base plate 130 of end effector assembly 100. As mentioned above, dissecting electrode 150 may be activated during advancement of end effector assembly 100 to facilitate dissection through tissue to reach the desired location. Further, end effector assembly 100 may be articulated, or rotated with respect to handle assembly 20, as discussed above, to better position end effector assembly 100 adjacent tissue "T" to be sealed and divided.

Once end effector assembly 100 is positioned adjacent tissue "T" to be sealed and divided, as shown in FIGS. 6A and 6B, switch 24 (or other control) (FIG. 1A) may be actuated to activate end effector assembly 100. Upon activation of end effector assembly 100, drive assembly 140 is activated to drive the rotation of gear members 110, 120 in the forward direction, i.e., such that gear members 110, 120 are rotating inwardly at feed-in side 135 of base plate 130, and/or to supply electrosurgical energy from electrosurgical cable 22, which extends through handle assembly 20 (see FIG. 1A), to sealing surface 114 of gear member 110 and/or sealing surface 124 of gear member 120, as discussed above. The activation of drive assembly 140 and the energization of sealing surface 114, 124 may be independently controlled, e.g., via separate switches 24, or may be commonly controlled, e.g., such that switch 24 (FIG. 1A) controls both the supply of electrosurgical energy and the activation of drive assembly 140. In either configuration, once end effector assembly 100 has been activated, end effector assembly 100 of surgical instrument 10 may be translated, lead by feed-in side 135 of base plate 130 toward tissue "T," i.e., in the direction of arrow "A."

Turning now to FIGS. 7A and 7B, upon further translation of end effector assembly 100 in the direction of arrow "A," gear members 110, 120 contact tissue "T." As shown in FIGS. 7A and 7B, tissue "T" is engaged by the cogs and recesses of the inwardly rotating gear members 110, 120 and is fed-in, or drawn into the gap "g" defined between gear members 110, 120. In other words, as gear members 110, 120 are rotated, tissue "T" is engaged by gear members 110, 120 and translated relative to end effector assembly 100 from feed-in side 135 of base plate 130 toward feed-out side 136 of base plate 130.

Figure 8A:
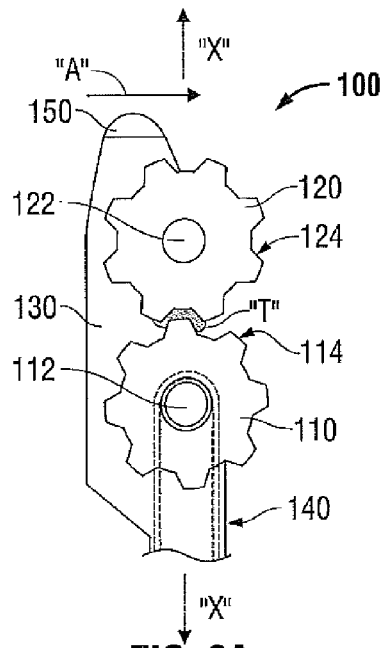
FIG. 8A is a side view of the end effector assembly of FIG. 4 shown with tissue to be sealed disposed between the gear members.
Figure 8B:
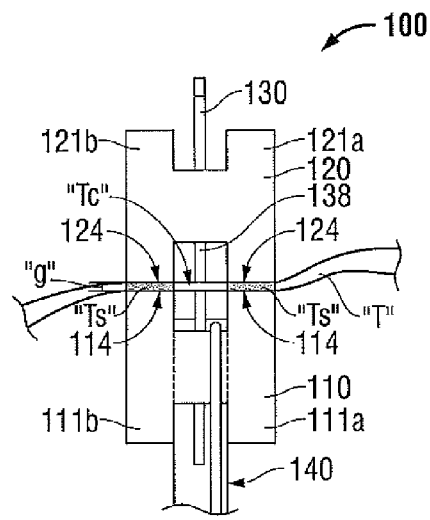
FIG. 8B is a top view of the end effector assembly of FIG. 4 shown with tissue to be sealed disposed between the gear members.
Figure 9A:
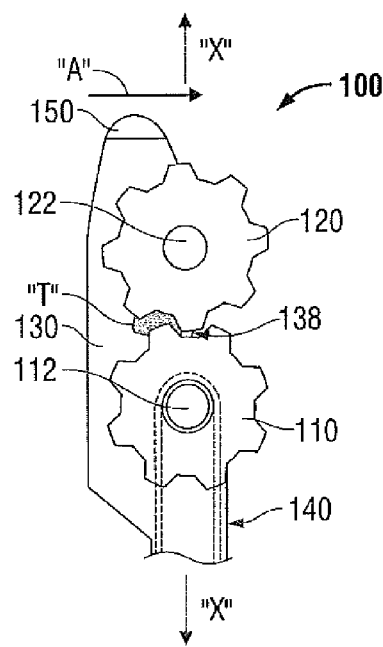
FIG. 9A is a side view of the end effector assembly of FIG. 4 where the sealed tissue disposed between the gear members has been divided.
Figure 9B:
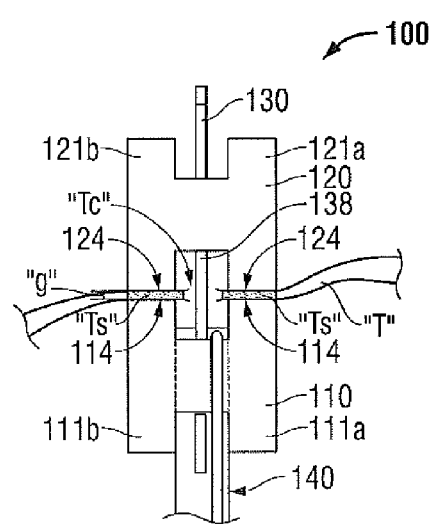
FIG. 9B is a top view of the end effector assembly of FIG. 4 where the sealed tissue disposed between the gear members has been divided.

As tissue "T" is fed further between gear members 110, 120, as shown in FIGS. 8A and 8B, tissue "T" is grasped, or clamped between gear members 110, 120 and, more specifically, between sealing surfaces 114, 124 of gear members 110, 120, respectively. As mentioned above, due to the electrical potential gradient between electrically-conductive sealing surfaces 114, 124 (which are energized to different electrical potentials upon activation of end effector assembly 100) of gear members 110, 120, respectively, electrosurgical energy is conducted through tissue disposed between gear members 110, 120.

The pressure exerted on tissue "T" by the meshed gear members 110, 120 and the gap distance "g" between sealing surfaces 114, 124, along with the electrosurgical energy conducted through tissue "T" cooperate to effect an adequate tissue seal of the portion of tissue "T" grasped between sealing surfaces 114, 124 of gear members 110, 120, respectively. More specifically, a gap distance within the range of about 0.001 inches to about 0.008 inches between sealing surfaces 114, 124 of gear members 110, 120 during tissue sealing is preferable to achieve an effective tissue seal, although other gap ranges may be preferable depending on the size and/or composition of tissue to be sealed. The pressure exerted on tissue "T" by the meshed gear members 110, 120 may be in the range of about 3 kg/cm$^2$ to about 16 kg/cm$^2$ to achieve an effective tissue seal although, as mentioned above, it may be desirable to exert a pressure on tissue "T" outside of this range, depending on the size and/or composition of tissue to be sealed. Accordingly, base plate 130 and gear members 110, 120 may be configured such that the gap distance "g" between sealing surfaces 114, 124 and the pressure exerted on tissue "T" grasped therebetween are within the above-identified ranges. Additionally, flexibility or compliance features associated with gear members 110, 120 and/or base plate 130, such as those discussed above with respect to base plate 130' (FIG. 3), may be provided to maintain the gap distance "g" and pressure on tissue within the above-identified ranges for sealing tissues of varying sizes and/or compositions.

As best shown in FIG. 8B, two separate tissue segments "Ts" of tissue "T" are sealed between sealing surfaces 114, 124 of gear members 110, 120, respectively: the tissue segment "Ts" disposed between sealing surfaces 114, 124 of gear halves 111a, 121a of gear members 110, 120, respectively, and the tissue segment "Ts" disposed between sealing surfaces 114, 124 of gear halves 111b, 121b of gear members 110, 120, respectively. As will be described below, tissue "T" is then divided, or cut across tissue segment "Tc," which is disposed between the sealed tissue segments "Ts."

Figure 10A:
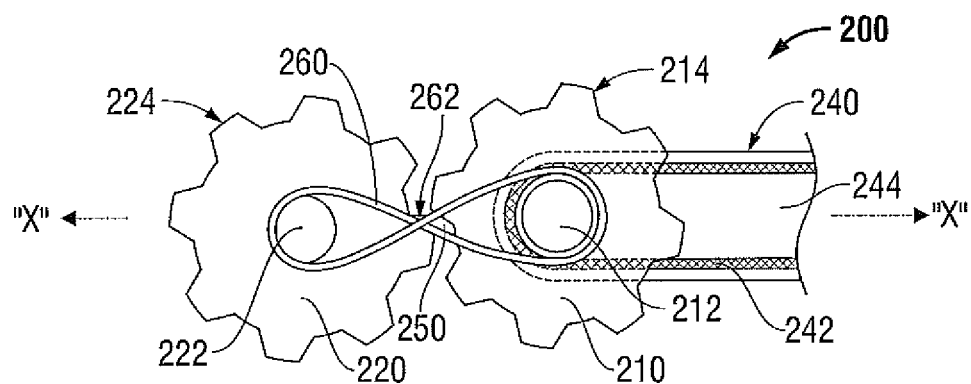
FIG. 10A is a side, cross-sectional view of another embodiment of an end effector assembly for use with the surgical instrument of FIG. 1A.
Figure 10B:
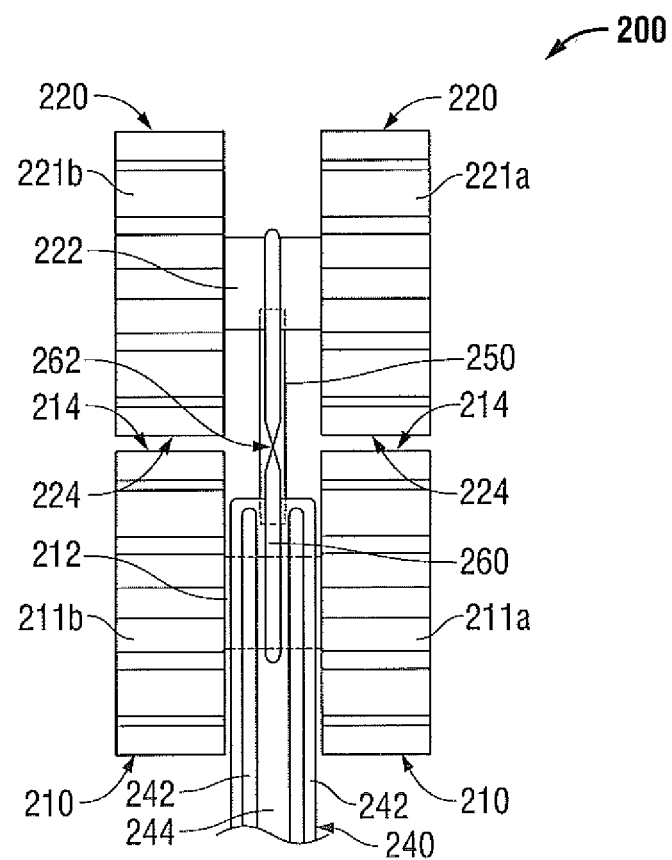
FIG. 10B is a top view of the end effector assembly of FIG. 10A.

Turning now to FIGS. 9A-9B and 10A-10B, upon further rotation of gear members 110, 120, sealed tissue "T" is further translated with respect to end effector assembly 100 toward feed-out side 136 of base plate 130 by the rotating gears 110, 120. Eventually, tissue "T," and more specifically, tissue segment "Tc," is urged into contact with cutting edge 138 of base plate 130, which is disposed between gear members 110, 120. Thus, upon further translation, or urging of tissue "T," e.g., due to the rotating gear members 110, 120, cutting edge 138 is advanced through tissue segment "Tc" of tissue "T," cutting or dividing tissue "T" between the two sealed tissue segments "Ts" and allowing the sealed and divided tissue "T" to pass on either side of base plate 130, as best shown in FIGS. 10A and 10B. As can be appreciated, tissue "T" is eventually disengaged, or fed-out of gear members 110, 120, as gear members 110, 120 are rotated outwardly at feed-out side 136 of base plate 130 of end effector assembly 100.

As described above, end effector assembly 100 is capable of feeding-in, or engaging tissue between gear members 110, 120, sealing tissue disposed between gear members 110, 120, cutting tissue along the previously-formed tissue seal with cutting edge 138 of base plate 130, and feeding-out, or releasing the sealed and divided tissue in one continuous process (as opposed to separate grasping, sealing and dividing steps). After tissue is sealed and divided, end effector assembly 100 may be advanced into position adjacent the next portion of tissue to be sealed and divided and the process can be repeated without requiring end effector assembly 100 to be reset or reconfigured, or otherwise modified. Thus, as can be appreciated, surgical instrument 10 can be used for efficiently sealing and dividing tissue (or multiple portions of tissue) in one continuous step. Further, the continuous feed-in, seal, cut, and feed-out feature of end effector assembly 100 can be used to seal and divide tissue of substantial length. In such an operation, end effector assembly 100 is advanced through tissue, continuously engaging, sealing and dividing tissue as it is fed between gear members 110, 120. In other words, due to this continuous-feed configuration, the length of tissue to be sealed and divided is not limited by the dimensions of end effector assembly 100.

Alternatively, where it is only desired to divide, or cut tissue, the above-describe process may be followed without activating, or supplying electrosurgical energy to gear members 110, 120. In such an embodiment, tissue is simply fed-in, or grasped between the rotating gear members 110, 120 and is advanced toward feed-out side 136 of base plate 135 by the rotating gear members 110, 120, eventually contacting cutting edge 138 of base plate 130 which divides tissue as it passes therethrough. Accordingly, surgical instrument 10 may also be used for safely, effectively and accurately dividing tissue (or multiple portions of tissue). In particular, as discussed above regarding the sealing and dividing mode, surgical instrument 10 may be used to divide tissue of substantial length due to the continuous feed feature of end effector assembly 100. In order to divide a large portion of tissue, end effector assembly is advanced along the cut-line such that tissue is continuously engaged by gear members 110, 120, cut, or divided therebetween, and then disengaged, or released from gear members 110, 120. Cutting may be effected mechanically, electrically, or by a combination of both. During cutting along cutting edge 138, the risk of damage to surrounding tissue is greatly reduced in that cutting edge 138 is only exposed to tissue disposed between gear members 110, 120.

Referring now to FIGS. 10A-10B, another embodiment of an end effector assembly, end effector assembly 200, configured for use with surgical instrument 10 is shown. End effector assembly 200 is similar to end effector assembly 100 (see FIGS. 1A-9B) and generally includes first and second gear members 210, 220 positioned end-to-end with respect to one another along longitudinal axis "X-X." Each gear member 210, 220 includes a pair of gear halves 211a, 211b and 221a, 221b, respectively, disposed on opposing ends of respective gear axles 212, 222. Gear members 210, 220 further define electrically-conductive sealing surfaces 214, 224, disposed on outer circumferential surfaces thereof that are adapted to connect to a source of electrosurgical energy (not shown). Gear member 210 is coupled to a drive assembly 240 for driving the rotation of one or both of gear members 210, 220. Drive assembly 240 is similar to drive assembly 140 of end effector assembly 100 (see FIGS. 4-5) and includes one or more drive cables 242 disposed within a drive shaft 244.

As opposed to end effector assembly 100, end effector assembly 200 includes a connecting shaft 250 (FIG. 10B), rather than a base plate, that couples gear members 210, 220 to one another and fixes the relative position of gear member 210 with respect to gear member 220 (while permitting rotation of gear members 210, 220), although end effector assembly 200 may also include a base plate as described above. Further, a cutting belt 260 is disposed about axles 212, 222 of gear members 210, 220, respectively, for dividing, or cutting tissue grasped between gear members 210, 220. Cutting belt 260 may further be configured to drive gear member 220, in embodiments where only gear member 210 is driven by drive assembly 240, or vice versa. The orientation of cutting belt 260 at gear member 210 may be rotated 180 degrees with respect to the orientation of cutting belt 260 at gear member 220 such that, as shown in FIG. 10A, cutting belt 260 defines a cross-over portion 262. Gear members 210, 220 and cutting belt 260 are configured such that the cross-over portion 262 extends between gear members 210, 220. As will be described below, tissue fed between gear members 210, 220 is divided by cutting belt 260, at, or in close proximity to cross-over portion 262. Connecting shaft 250 is positioned behind, cutting belt 260, when viewed from the feed-in side of end effector assembly 200 such that, as can be appreciated, connecting shaft 250 does not interfere with cutting blade 260 during tissue division.

Figure 11A:
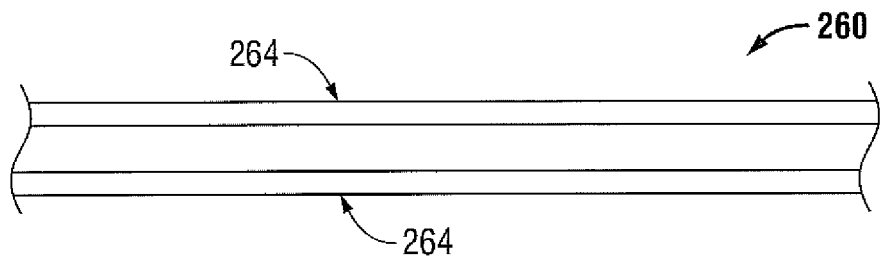
FIG. 11A is a side view of one embodiment of a cutting belt for use with the end effector assembly of FIG. 10A.
Figure 11B:
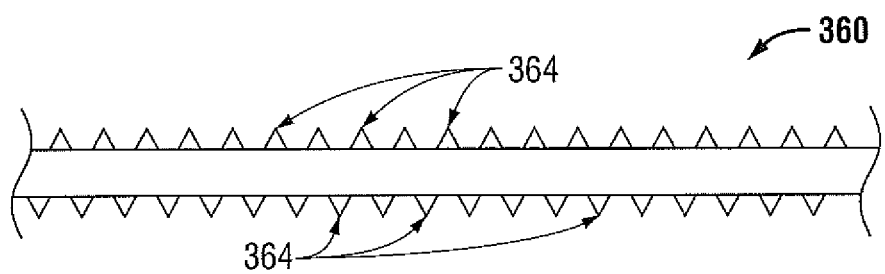
FIG. 11B is a side view of another embodiment of a cutting belt for use with the end effector assembly of FIG. 10A.
Figure 11C:
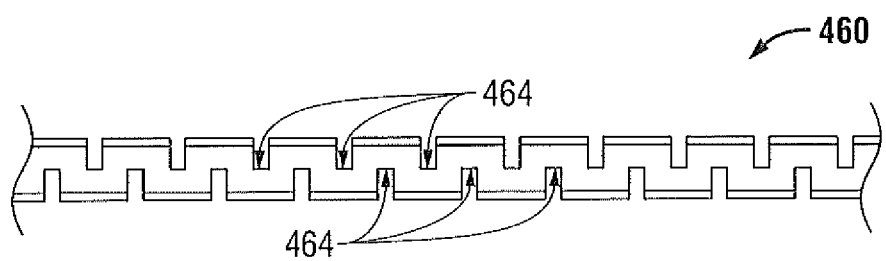
FIG. 11C is a side view of yet another embodiment of a cutting belt for use with the end effector assembly of FIG. 10A.

Turning now to FIGS. 11A-11C, various configurations of the cutting belt 260 are shown. As shown in FIG. 11A, cutting belt 260 may define generally straight, opposed cutting edges 264. Alternatively, as shown in FIG. 11B, the cutting belt 360 may include serrations 364 defined therealong. Additionally, or alternatively, the cutting belt 460 may include notches 464 or other features (not shown) allowing cutting belt 460 to expand and contract in response to the forces acting on cutting belt 460, thereby reducing the likelihood of belt misalignment or damage to the cutting belt.

Referring once again to FIGS. 10A-10B, the use and operation of end effector assembly 200 is substantially similar to that of end effector assembly 100, described above, and, thus, will only be summarized here. Initially, end effector assembly 200 is positioned adjacent tissue to be sealed and divided. Drive assembly 240 and sealing surfaces 214, 224 are then activated such that gear members 210, 220 are driven, or rotated in meshed engagement with one another and such that sealing surfaces 214, 224 are energized with electrosurgical energy (to different electrical potentials). Cutting belt 460 may be configured to rotate along with gear members 210, 220, or may be configured to remain stationary during rotation of gear members 210, 220.

With end effector assembly 200 activated, gear members 210, 220 are translated toward tissue to be sealed and divided. As gear members 210, 220 contact tissue, tissue is fed-in, or engaged by gear members 210, 220. The tissue is further translated through the gap defined between gear members 210, 220 by the rotation of gear members 210, 220. At the same time, electrosurgical energy is conducted between sealing surfaces 214, 224 of gear members 210, 220 and through tissue disposed therebetween to effect a tissue seal.

Upon further rotation of gear members 210, 220 and, thus, upon further translation of tissue with respect to end effector assembly 200, tissue contacts cutting belt 460, and, more specifically, cross-over portion 462 of cutting belt 460, which cuts through tissue, dividing tissue along the previously-formed tissue seal. As mentioned above, cutting belt 460 may be configured to rotate along with gear members 210, 220 to facilitate dividing of tissue disposed between gear members 210, 220, e.g., to create a multi-directional dynamic cutting effect (due to the rotation of each segment making up cross-over portion 462 in opposite directions). The serrated cutting belt 360 is particularly adapted for use during dynamic cutting, i.e., where cutting belt 360 is rotating along with gear members 110, 120, creating a saw-like cutting effect. Alternatively, cutting belt 460 may remain rotationally stationary as it is advanced through tissue.

As discussed above with respect to end effector assembly 100, the sealed and divided tissue is eventually disengaged, or released from the rotating gear members 210, 220. The process may be subsequently repeated for sealing and dividing additional portions of tissue. Further, as in the previous embodiment, end effector assembly 200 may be used to simply cut, or divide tissue, in which case sealing surfaces 214, 224 of gear members 210, 220, respectively, would not be energized with electrosurgical energy during the cutting process.

Figure 12A:
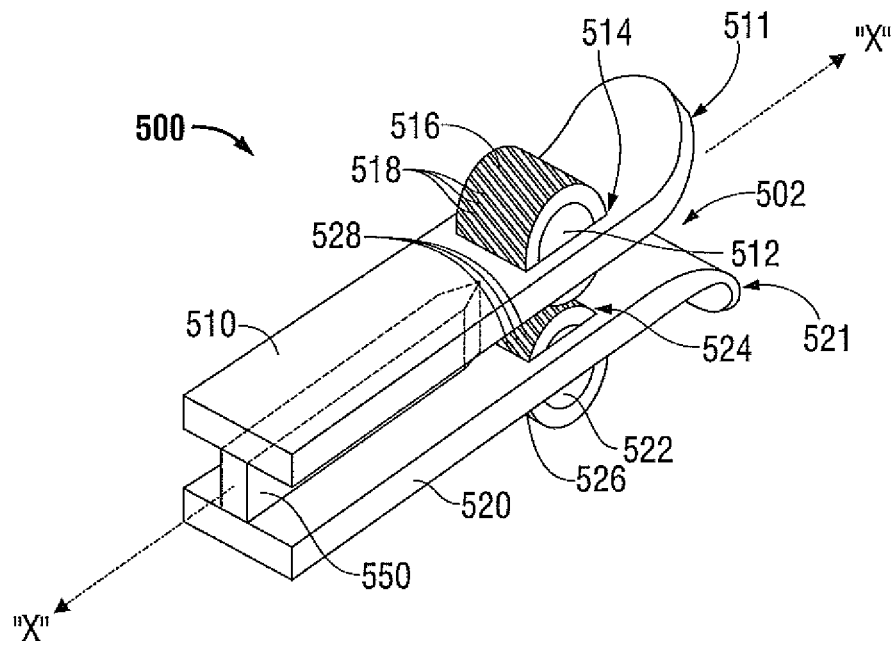
FIG. 12A is a perspective view of another embodiment of an end effector assembly in accordance with the present disclosure.
Figure 12B:
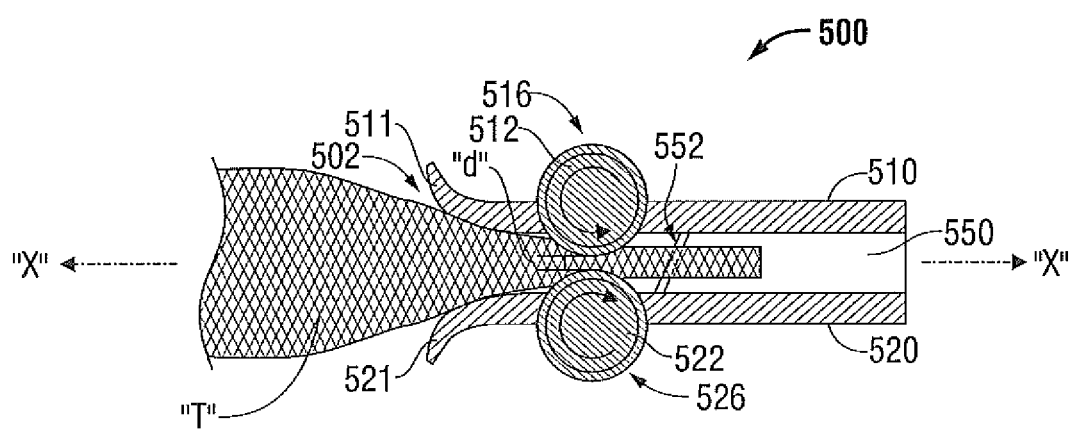
FIG. 12B is a side, cross-sectional view of the end effector assembly of FIG. 12A.

With reference now to FIGS. 12A and 12B, another embodiment of an end effector assembly 500 for continuously sealing and/or dividing tissue is shown. End effector assembly 500 is similar in operation to end effector assemblies 100, 200 discussed above (see FIGS. 4 and 10A, respectively). As in the previous embodiments, end effector assembly 500 may be coupled to a handle assembly 20 (FIG. 1A) via an elongated shaft 30 (FIG. 1A), although end effector assembly 500 need not be used with a shaft-based instrument. End effector assembly 500 defines a longitudinal axis "X-X" and includes a pair of opposed base plates 510, 520 fixedly disposed in a spaced-apart relation relative to one another. One or both of base plates 510, 520 may include an arcuate distal end 511, 521, respectively, that curves off of, or away from longitudinal axis "X-X" to define a funnel-shaped "feed-in" side 502 of end effector assembly 500 such that tissue "T" is funneled, or urged between base plates 510, 520 upon distal advancement of end effector assembly 500 with respect to tissue "T." Each base plate 510, 520 further includes a wheel, or gear member 512, 522, respectively, rotatably mounted thereon. More specifically, as best shown in FIG. 12A, wheels 512, 522 may be rotatably mounted within respective cut-out portions 514, 524 of base plates 510, 520. Wheels 512, 522 are disposed in a spaced-apart relation relative to one another on opposing sides of longitudinal axis "X-X" to define a gap distance "d" therebetween. A knife 550 positioned proximally of wheels 512, 522 is fixedly disposed between base plates 510, 520 and extends along longitudinal axis "X-X" to defining a cutting edge 552 for cutting tissue "T" disposed between base plates 510, 520, as will be described below.

As in the previous embodiments, each wheel 512, 522 may be coupled to a drive assembly 140 (FIG. 4) for driving the rotation of wheels 512, 522, although wheels 512, 522 may be configured to simply rotate, or roll over tissue "T" without the use of a powered drive assembly. Alternatively, wheels 512, 522 may be disposed in meshed engagement such that rotation of one of wheels 512, 522 effects rotation of the other wheel 512, 522. In such an embodiment, only one of wheels 512, 522 need be coupled to drive assembly 140 (FIG. 4) for rotating wheels 512, 522. In either embodiment, wheels 512, 522 are configured to rotate inwardly toward longitudinal axis "X-X," when viewed from feed-in side 502 of end effector assembly 500, as best shown in FIG. 12B, such that tissue "T" is grasped by wheels 512, 522 and is fed-between wheels 512, 522 as end effector assembly 500 is advanced distally through tissue "T." However, wheels 512, 522 may also be configured to operate in a reverse-mode, wherein wheels 512, 522 rotate in the opposite direction.

With continued reference to FIGS. 12A and 12B, one or both of wheels 512, 522 may be coupled to a source of electrosurgical energy for sealing tissue "T" disposed therebetween. Wheels 512, 522 may each include an electrically-conductive tissue sealing plate 516, 526 disposed on an outer circumferential surface thereof (or may define a outer-circumferential electrically-conductive sealing surface) such that energy supplied to wheels 512, 522 may be conducted between sealing plates 516, 526 and through tissue "T" disposed therebetween for sealing tissue "T" grasped between wheels 512, 522. Alternatively, or additionally, energy may be supplied to selective portions, e.g., zones, of base plate 510 and/or base plate 520 such that energy may be conducted through sealing plates 516, 526 and/or through knife 550. Knife 550 may thus be configured for mechanical cutting, electrical cutting, or any combination thereof and may further include energizeable and/or insulated surfaces to achieve this mechanical and/or electrical cutting effect. The sealing plates 516, 526 may also include grasping/textured features, e.g., ridges 518, 528, respectively, to facilitate grasping of tissue "T" upon rotation of wheels 512, 522.

In use, end effector assembly 500 is initially positioned such that tissue "T" to be sealed and divided is disposed adjacent "feed-in" side 502 of end effector assembly 500, i.e., such that tissue "T" is positioned adjacent distal ends 511, 521 of base plates 510, 520, respectively. End effector assembly 500 is then activated. Upon activation of end effector assembly 500, the drive assembly (not shown) is activated to drive the rotation of wheels 512, 522 such that wheels 512, 522 rotate inwardly toward longitudinal axis "X-X" when viewed from feed-in side 502 of end effector assembly 500.

Electrosurgical energy may also be supplied to one or both sealing plates 516, 526 of wheels 512, 522, respectively, to create an electrical potential gradient therebetween upon activation of end effector assembly 500, although the activation of the drive assembly (not shown) and the energization of sealing plates 516, 526 may be independently controlled.

Once end effector assembly 500 is positioned as described above and activated, end effector assembly 500 may be translated distally, led by feed-in side 502, toward tissue "T." As end effector assembly 500 is advanced toward tissue "T," tissue "T" is fed between base plates 510, 520, i.e., tissue "T" is fed into the "feed-in" side 502 of end effector assembly 500. As mentioned above, the funnel-shaped configuration of distal ends 511, 521 of base plates 510, 520, respectively, urges tissue "T" between base plates 510, 520 as end effector assembly 500 is advanced distally.

Upon further distal translation of end effector assembly 500, wheels 512, 522 contact tissue "T." As wheels 512, 522 contact tissue "T," tissue "T" is engaged by sealing plates 516, 526 of the inwardly rotating wheels 512, 522, respectively, e.g., due to ridges 518, 528 defined on sealing plates 516, 526, respectively, or other grasping/textured features, and is fed-in, or drawn into the gap "d" defined between wheels 512, 522. In other words, as wheels 512, 522 are rotated, tissue "T" is engaged within and translated proximally relative to end effector assembly 500 from feed-in side 502 thereof toward knife 550 that is disposed proximally of wheels 512, 522. As tissue "T" is fed further between wheels 512, 522, as best shown in FIG. 12B, tissue "T" is grasped between sealing plates 516, 526 of wheels 512, 522, respectively. At the same time, due to the electrical potential gradient between sealing plates 516, 526 (which are energized to different electrical potentials upon activation of end effector assembly 500), electrosurgical energy is conducted through tissue "T" to effect a tissue seal.

The pressure exerted on tissue "T" by wheels 512, 522, and the gap distance "d" between sealing plates 516, 526, along with the electrosurgical energy conducted through tissue "T" cooperate to effect an adequate tissue seal of the portion of tissue "T" grasped between sealing plates 516, 526 of wheels 512, 522, respectively. As stated above, a gap distance within the range of about 0.001 inches to about 0.008 inches between sealing plates 516, 526 of wheels 512, 522 during tissue sealing is preferable to achieve an effective tissue seal, although other gap ranges are also contemplated. The pressure exerted on tissue "T" by wheels 512, 522 may be in the range of about 3 kg/cm$^2$ to about 16 kg/cm$^2$ to achieve an effective tissue seal although, as mentioned above, it may be desirable to exert a pressure on tissue "T" outside of this range, depending on the size and/or composition of tissue to be sealed. Accordingly, base plates 510, 520 and respective wheels 512, 522 may be positioned such that the gap distance "d" between sealing plates 516, 526 and the pressure exerted on tissue "T" grasped therebetween are within the above-identified ranges. Additionally, base plates 510, 520 may be moveable with respect to one another to vary the gap distance "d" between sealing plates 516, 526 and/or the pressure exerted on tissue "T" for sealing tissues of varying sizes and/or compositions.

Upon further rotation of wheels 512, 522, sealed tissue "T" is further translated proximally between base plates 510, 520 toward knife 550 by the rotating wheels 512, 522, i.e., tissue "T" is fed-out from the rotating wheels 512, 522. Eventually, tissue "T" is urged into contact with cutting edge 552 of knife 550. Further translation, or urging of tissue "T," e.g., due to the rotating wheels 512, 522, advances cutting edge 552 through tissue "T," cutting or dividing tissue "T" along the previously-formed tissue seal. Thus, as can be appreciated, end effector assembly 500 is capable of grasping and sealing tissue "T" between wheels 512, 522, cutting tissue "T" along the previously-formed tissue seal, and releasing the sealed and divided tissue "T" in one continuous process (as opposed to separate grasping, sealing and dividing steps). After tissue "T" is sealed and divided, the above-mentioned process can be repeated without requiring end effector assembly 500 to be reset, reconfigured, or otherwise modified. Further, the continuous feed-in, seal, feed-out and cut process allows end effector assembly 500 to be used for continuously sealing and/or dividing large portions of tissue as the tissue is fed through wheels 512, 522.

Figure 13:
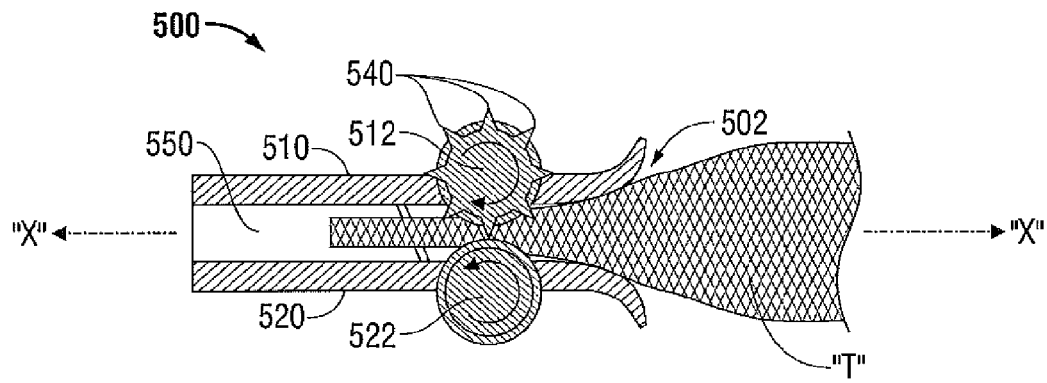
FIG. 13 is a side, cross-sectional view of the end effector assembly of FIG. 12A including a plurality of perforating barbs disposed on a wheel of the end effector assembly.

Turning now to FIG. 13, wheel 512 of end effector assembly 500 (and/or wheel 522 of end effector assembly 500) may include a plurality of perforating barbs 540 disposed on an outer circumference thereof. As wheels 512, 522 are rotated to grasp and seal tissue "T" therebetween, barbs 540 perforate tissue "T" to facilitate tissue sealing. More particularly, barbs 540 perforate tissue "T" grasped between wheels 512, 522 to intensify collagen and elastin release during tissue sealing. Other perforating features for facilitating tissue sealing are also contemplated. Perforating features may also be used for partial or complete cutting of tissue, without the need for a knife 550.

Figure 14:
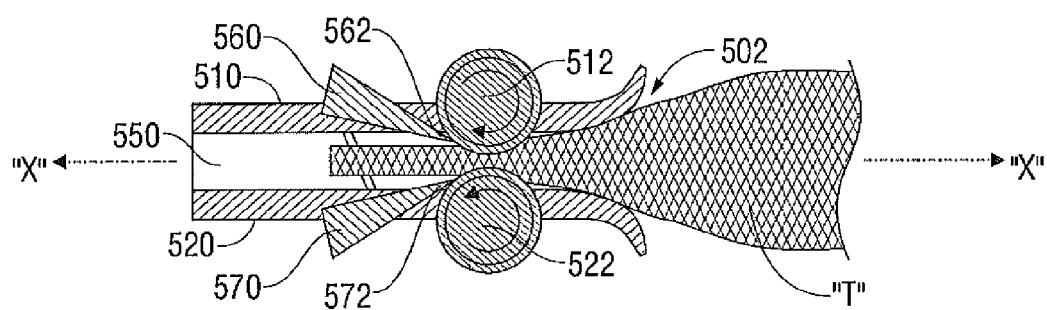
FIG. 14 is a side, cross-sectional view of the end effector assembly of FIG. 12A including a pair of cleaning blades disposed on the end effector assembly.

FIG. 14 shows end effector assembly 500 including a pair of cleaning blades 560, 570 disposed on base plates 510, 520, respectively, and positioned proximal of wheels 512, 522, respectively. Cleaning blades 560, 570 include distal tip portions 562, 572 disposed adjacent to sealing plates 516, 526 of wheels 512, 522, respectively. Cleaning blades 560, 570 inhibit tissue "T" from sticking, or adhering to sealing plates 516, 526. More specifically, as wheels 512, 522 are rotated to seal tissue "T" and urge tissue "T" proximally toward knife 550, distal tip portions 562, 572 scrape-off, or peel-off tissue "T" from sealing plates 516, 526, thereby reducing the likelihood of tissue damage, e.g., tearing of tissue and compromising the previously-formed tissue seal. Further, cleaning blades 560, 570 inhibit tissue "T" from accumulating on sealing plates 516, 526 and from interfering with the rotation of wheels 512, 522.

Figure 15:
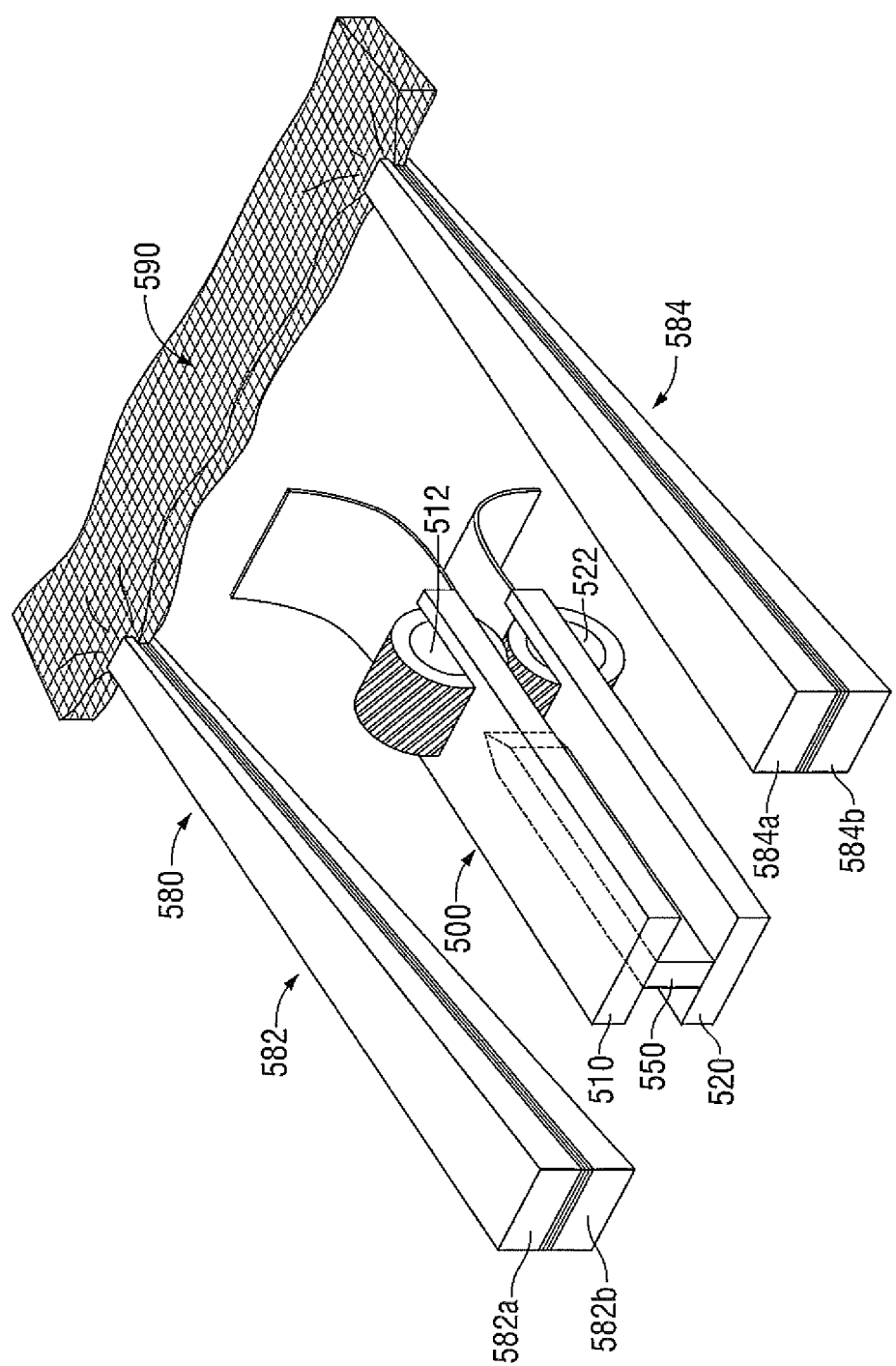
FIG. 15 is a perspective view of the end effector assembly of FIG. 12A shown configured for use with a grasping assembly.

Turning now to FIG. 15, end effector assembly 500 is shown configured for use with a grasping assembly 580. Grasping assembly 580 include two sets of jaw members: a first pair of jaw members 582 and a second pair of jaw members 584, although only one pair of jaw members 582, 584 may be provided. Each pair of jaw members 582, 584 includes upper and lower jaw components 582a, 582b and 584a, 584b, respectively. As can be appreciated, each pair of jaw members 582, 584 is moveable between a spaced-apart position and an approximated position for grasping tissue 590 therebetween, i.e., components 582a, 582b (collectively jaw members 582) are moveable with respect to one another and components 584a, 584b (collectively jaw members 584) are moveable with respect to one another to move jaw members 582, 584, respectively, between the spaced-apart and approximated positions. More specifically, when moved to the approximated position, jaw member pairs 582, 584 are configured to grasp tissue 590 to be sealed and/or divided at two positions: between components 582a and 582b, e.g., between jaw members 582, and between components 584a and 584b, e.g., between jaw members 584, with suspended tissue 590 extending between jaw member pairs 582, 584. In other words, grasping assembly 580 retains tissue 590 in a fixed position such that the end effector assembly 500 may be translated between jaw member pairs 582, 584 and with respect to tissue 590, as described above, for sealing and/or dividing tissue 590.

Figure 16:
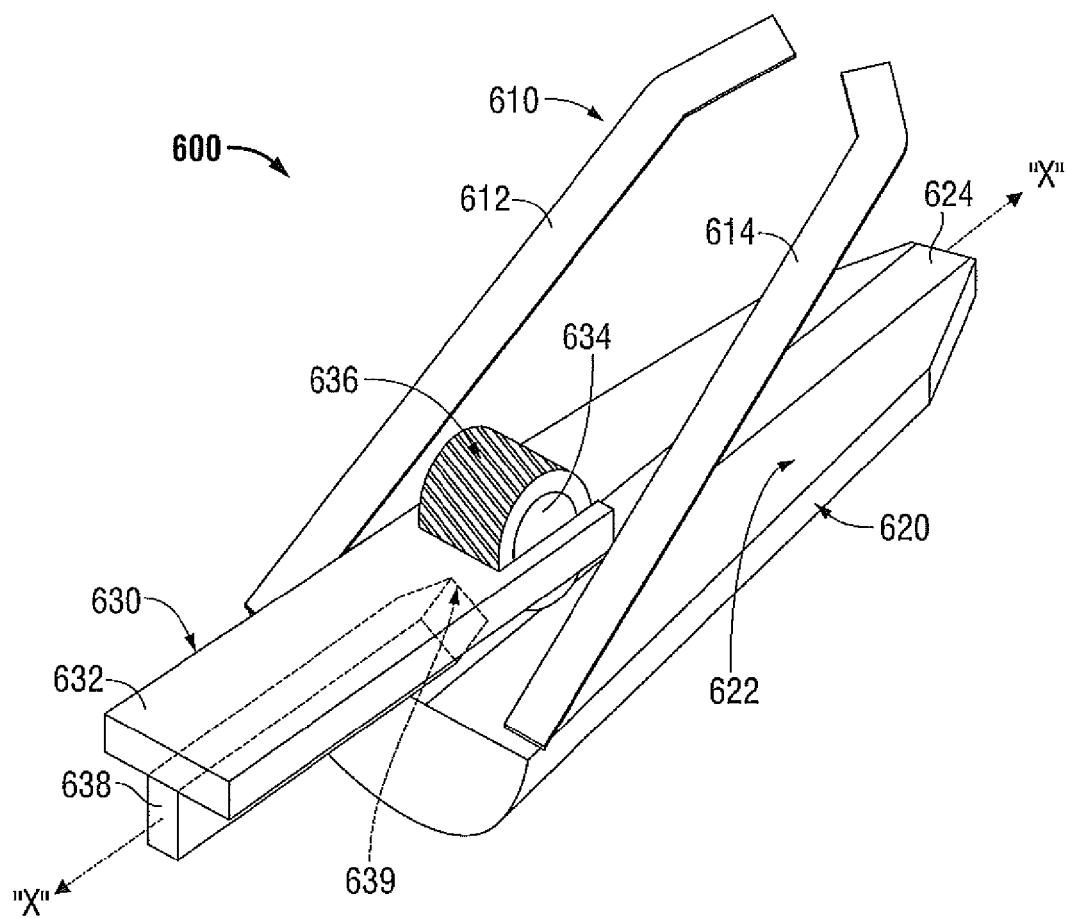
FIG. 16 is a perspective view of yet another embodiment of an end effector assembly in accordance with the present disclosure.

With reference now to FIG. 16, yet another embodiment of an end effector assembly, end effector assembly 600, for sealing and dividing tissue is shown. As in the previous embodiments, end effector assembly 600 may be configured for use with a shaft-based instrument. End effector assembly 600 defines a longitudinal axis "X-X" and includes first and second jaw members 610, 620 disposed in opposed relation relative to one another and moveable with respect to one another between a spaced-apart position and an approximated position for grasping tissue therebetween. First jaw member 610 includes first and second arms 612, 614, while second jaw member 620 defines an opposed surface 622 having an electrically-conductive tissue sealing strip 624 extending longitudinally therealong. Strip 624 may be coupled to a source of electrosurgical energy (not shown). Upon approximation of jaw members 610, 620, arms 612, 614 of jaw member 610 grasp tissue between each of arms 612, 614 and opposed surface 622 of jaw member 620 on either side of tissue sealing strip 624.

End effector assembly 600 further includes a wheel assembly 630. Wheel assembly 630 is configured for longitudinal translation between jaw members 610, 620 to seal and divide tissue grasped therebetween. Wheel assembly 630 includes a base 632 having a wheel 634 mounted thereon. Wheel 634, similar to wheels 512, 522 of end effector assembly 500, is rotatably mounted to base 632 and includes an electrically conductive sealing plate 636 disposed on a circumferential surface thereof that is adapted to connect to a source of electrosurgical energy. A drive assembly (not shown) may be provided for driving the rotation of wheel 634 or, alternatively, wheel 634 may be configured to roll-over tissue during translation of wheel assembly 630, without the use of a drive assembly (not shown). Wheel 634 of wheel assembly 630 is aligned with strip 624 of jaw member 620 such that, upon distal translation of wheel assembly 630 between jaw members 610, 620, wheel 634 is translated along strip 624 (and is rotated with respect to strip 624). Accordingly, electrically conductive sealing plate 636 of wheel 634 and strip 624 of jaw member 620 may be energized to different electrical potentials for conducting electrosurgical energy therebetween to seal tissue grasped between jaw members 610, 620 upon translation of wheel 634 along strip 624 of jaw member 620.

Base 632 of wheel assembly 630 further includes a knife 638 fixedly disposed on a lower surface thereof and extending longitudinally therealong. Knife 638 includes a cutting edge 639 positioned adjacent to and proximal of wheel electrode 634 for cutting sealed tissue, as will be described below. Knife 638 also maintains the gap distance between electrically conductive sealing plate 636 of wheel 634 and electrically conductive strip 624 of jaw member 620 as wheel assembly 630 is translated between jaw members 610, 620 during tissue sealing.

In use, with jaw members 610, 620 in the spaced-apart position, end effector assembly 600 is positioned such that tissue to be sealed and/or divided is disposed between jaw members 610, 620. Jaw members 610, 620 are then moved to the approximated position to grasp tissue therebetween. More particularly, tissue is grasped between arm 612 of jaw member 610 and opposed surface 622 of jaw member 620 on a first side of strip 624 and between arm 614 of jaw member 610 and opposed surface 622 of jaw member 620 on a second side of strip 624. With tissue grasped between jaw members 610, 620, wheel assembly 630 is translated distally along longitudinal axis "X-X" with respect to jaw members 610, 620 and tissue grasped therebetween. Simultaneously, wheel 634 is rotated and electrosurgical energy is supplied to sealing plate 636 and/or strip 624 to create an electrical potential gradient therebetween. As wheel assembly 630 is advanced further, wheel 634 eventually contacts tissue grasped between jaw members 610, 620, and rolls over tissue as electrosurgical energy is conducted between sealing plate 636 and strip 624 and through tissue to effect a tissue seal. As can be appreciated, relatively large portions of tissue may be sealed as wheel assembly 630 is translated along the length of jaw member 620, rotating, or rolling over tissue.

Once wheel 634 rolls and translates distally over tissue grasped between jaw members 610, 620 to seal tissue, further distal translation of wheel assembly 630 causes knife 638 to be advanced through the previously-sealed tissue, cutting, or dividing the sealed tissue. Thus, where larger portions of tissue are grasped between jaw members 610, 620, the tissue is continuously sealed and divided as wheel assembly 630 is advanced therethrough. End effector assembly 600 otherwise functions similar to end effector assembly 500 discussed above, except that only one wheel 634 is provided, with conductive strip 624 of jaw member 620 replacing the second wheel. Accordingly, the gap distance and tissue pressures ranges as well as the additional features discussed above are similarly applicable to end effector assembly 600. Alternatively, end effector assembly 600 may be configured for use without arms 612, 614. Further, knife 638 may be configured to move independently of wheel assembly 630 for selectively cutting tissue independent of the advancement of wheel assembly 630.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed:

1. A surgical instrument, comprising:
   an end effector assembly defining a feed-in side, the end effector assembly including first and second rotatable gear members positioned adjacent one another to define a gap therebetween, wherein, when the first and second gear members are rotated, tissue positioned adjacent the feed-in side of the end effector assembly is engaged by the first and second gear members and is fed into the gap between the first and second gear members for at least one of sealing and dividing tissue disposed between the first and second gear members, the first and second gear members meshed with one another such that rotation of the first gear member effects rotation of the second gear member.

2. The surgical instrument according to claim 1, wherein at least one of the first and second gear members is adapted to connect to a source of electrosurgical energy such that energy is conducted between the gear members and through tissue disposed therebetween to effect a tissue seal.

3. The surgical instrument according to claim 1, wherein at least one of the gear members includes an electrically-insulative material disposed on at least a portion of an outer periphery thereof to maintain the gap defined between the first and second gear members.

4. The surgical instrument according to claim 1, wherein the first and second gear members define complementary outer peripheral configurations.

5. The surgical instrument according to claim 1, further comprising a base plate interconnecting the first and second gear members.

6. The surgical instrument according to claim 5, wherein the base plate defines a cutting edge extending between the first and second gear members for cutting tissue disposed therebetween.

7. The surgical instrument according to claim 6, wherein the base plate includes a dissecting distal tip adapted to connect to a source of electrosurgical energy.

8. The surgical instrument according to claim 1, further comprising a handle assembly having a shaft extending distally therefrom, wherein the end effector assembly is disposed at a distal end of the shaft.

9. The surgical instrument according to claim 8, wherein the end effector assembly is articulatable with respect to the shaft.

10. The surgical instrument according to claim 1, further comprising a drive assembly coupled to at least one of the first and second gear members for rotating the first and second gear members.

11. The surgical instrument according to claim 10, wherein the drive assembly includes a drive cable coupled to an axle of the first gear member for rotating the first gear member in at least one of a forward and a reverse direction.

12. The surgical instrument according to claim 1, further comprising a cutting belt disposed between the first and second gear members and positioned about axles of the first and second gear members, the cutting belt configured for cutting tissue disposed between the gear members.

13. The surgical instrument according to 1, wherein the gap between the first and second gear members defines a length in the range of about 0.001 inches to about 0.008 inches.

14. The surgical instrument according to claim 1, wherein the first and second gear members are configured to exert a pressure on tissue grasped therebetween in the range of about 3 kg/cm$^2$ to about 16 kg/cm$^2$.

15. A surgical instrument, comprising:
   an end effector assembly defining a longitudinal axis and a feed-in side, the end effector assembly including:
      a base plate extending along the longitudinal axis and defining a proximal end and a distal end; and
      first and second gear members rotatably mounted on the base plate and configured for at least one of sealing and dividing tissue disposed between the first and second gear members;
      wherein the base plate is configured for at least one of maintaining the first and second gear members in a spaced-apart configuration relative to one another to define a gap distance therebetween and maintaining a pressure on tissue grasped between the gear members, and
      wherein the base plate includes at least one compliance feature configured for adjusting the gap distance between the gear members or the pressure exerted on tissue grasped between the gear members, according to a size or a composition of tissue grasped between the gear members.

16. The surgical instrument according to claim 15, wherein the first gear member is adapted to connect to a first electrical potential and wherein the second gear member is adapted to connect to a second electrical potential such that energy is conducted between the gear members and through tissue disposed therebetween to effect a tissue seal.

17. The surgical instrument according to claim 15, wherein the base plate defines a cutting edge extending between the first and second gear members for cutting tissue disposed therebetween.

18. The surgical instrument according to claim 15, wherein the base plate includes a dissecting distal tip adapted to connect to a source of electrosurgical energy.

19. The surgical instrument according to claim 15, further comprising a drive assembly coupled to at least one of the first and second gear members for rotating the first and second gear members.

20. The surgical instrument according to claim 15, wherein each of the first and second gear members defines a bifurcated configuration and wherein the base plate extends between each of the bifurcated gear members.

21. The surgical instrument according to claim 15, wherein the gap distance between the first and second gear members is in the range of about 0.001 inches to about 0.008 inches.

22. The surgical instrument according to claim 15, wherein the base plate is configured for maintaining the pressure exerted on tissue between the gear members is in the range of about 3 $kg/cm^2$ to about 16 $kg/cm^2$.

* * * * *